United States Patent [19]

Calhoun

[11] 4,391,372

[45] Jul. 5, 1983

[54] VACUUM STARWHEEL

[75] Inventor: Fredrick L. Calhoun, Rolling Hills, Calif.

[73] Assignee: Industrial Dynamics Company, Ltd., Torrance, Calif.

[21] Appl. No.: 893,243

[22] Filed: Apr. 3, 1978

Related U.S. Application Data

[63] Continuation of Ser. No. 738,824, Nov. 4, 1976, abandoned.

[51] Int. Cl.³ .............................................. B07C 5/00
[52] U.S. Cl. .................................. 209/523; 209/905; 198/370; 198/438
[58] Field of Search ............... 198/362, 366, 370, 372, 198/438, 441, 493, 494, 689; 209/73, 74 R, 111.7 T, 524–533, 905, 523

[56] References Cited

U.S. PATENT DOCUMENTS

| | | | |
|---|---|---|---|
| 2,800,226 | 7/1957 | Drennan | 198/441 |
| 3,275,136 | 9/1966 | Allen et al. | 209/74 R |
| 3,279,599 | 10/1966 | Drennan | 209/74 R |
| 3,485,357 | 12/1969 | Payne | 209/73 |
| 3,756,402 | 9/1973 | Wagers et al. | 209/73 |
| 3,782,523 | 1/1974 | Giatti | 198/438 |

Primary Examiner—Joseph E. Valenza
Attorney, Agent, or Firm—Charles H. Schwartz; Ellsworth R. Roston

[57] ABSTRACT

A vacuum starwheel which provides for a positive vacuum to hold containers, such as bottles, to maintain the bottles in position during transfer by the starwheel, and with the use of a pair of hub members, one rotating relative to the other, and with one hub member including a plurality of ports corresponding to and connecting with tubes and cups to retain the bottles and with the other hub including a plurality of ports connected to either vacuum, pressure or atmosphere, and with at least two of the ports being elongated, and with a first small port intermediate the two elongated ports and a second small port after the two elongated ports and with vacuum always applied to the two elongated ports, and with either vacuum, pressure or atmosphere, applied to the two small ports to either release a bottle at the intermediate position or to transfer the bottle along the entire length of the two elongated ports and then release the bottle.

23 Claims, 13 Drawing Figures

Fig. 8
MULTI-LANE PORTING ARRANGEMENT FOR STATIONARY HUB.

DIRECTION OF ROTATION OF PORT 72

VACUUM STARWHEEL

This is a continuation of application Ser. No. 738,824 filed Nov. 4, 1976 (now abandoned).

The present invention relates to a vacuum starwheel for diverting containers, such as bottles, into one of a number of conveyor lines. For example, it is a common practice to have a plurality of containers, such as bottles, moved down a conveyor line to a station for inspection of the container for either various types of defects or for segregation between different types of containers. The bottles enter into and are engaged by a vacuum starwheel which generally moves the bottles along a circular path with each bottle contained within a separate pocket to the starwheel and with the bottles then deposited onto a specific one of a plurality of outfeed lines in accordance with the previous inspection. For example, if the inspection is to determine contamination of the bottles, one outfeed line may represent rejects and another line may represent acceptable bottles. If, for example, the inspection is to segregate the containers, such as bottles, according to shape, one outfeed line may represent bottles of one shape and the other outfeed line may represent bottles of another shape or there may even be a plurality of outfeed line representing bottles of different shapes. In addition, the vacuum starwheel may be used merely to subdivide a large plurality of containers, such as bottles, from an infeed conveyor line to a plurality of outfeed conveyor lines.

Generally, the vacuum starwheel includes a plurality of suction cups each connected by a tube to a source of vacuum. Various combinations of applying vacuum or releasing vacuum to a particular suction cup determines the final destination of the container in contact with that cup.

As one particular example, a prior art system would apply vacuum through a suction cup to the container, such as a bottle, only if it is to be removed from the conveyor line. The bottle is held by the suction cup as it is transported by the starwheel for removal, through the use of a residual vacuum, while the remainder of the bottles continue down the conveyor line. In other words, a valve is opened to apply vacuum to a particular suction cup to hold the bottle to be removed and then the valve closed so that particular bottle is held by the residual suction present in the suction cup and the tubing and thus removed from the conveyor line. This type of system presents difficulties because there is not a continuous vacuum on the bottle that is being transported off the conveyor by the starwheel, and any leakage in the system can cause a line jam or lose the bottle that is being removed. Other types of prior art systems do provide for a positive vacuum on the bottle to be segregated, but use a separate valve for each bottle so as to apply the vacuum constantly during the segregation cycle by the starwheel. The use of a plurality of separate valves is relatively complicated and expensive and also provides for significant maintenance problems since all of these separate valves must be maintained in proper operating condition.

The present invention is directed to a vacuum starwheel which has positive control of the containers, such as bottles, at all times during the transfer and segregation of the bottles by the starwheel. However, the present invention eliminates the plurality of separate valves and has a very simple design using a stationary and rotating hub that contain commutating ports so arranged to provide a constant vacuum to each bottle in the starwheel unless it is to be segregated from the others on the conveyor line. If a particular bottle is to be segregated then the vacuum is removed, thus releasing that bottle from the starwheel at a particular position while all others remain in the starwheel and are released at some other position. Generally, the present invention provides for a very positive release of a bottle from the vacuum starwheel at a selected position during its rotation by interrupting the vacuum with a burst of pressure. The starwheel hub can be designed to accept bottles from a single infeed and segregate them into two or more outfeed positions. Additionally, the present invention can provide for a pressure purge of each port, pipe and suction cup during every rotation of the starwheel so as to clear these parts of any debris.

Specifically, the present invention relates to a vacuum sorting mechanism for transferring containers from at least one infeed position to any one of at least two independent outfeed positions and including a rotary member including at least one rotating port and a corresponding radially extended vacuum directing and holding means that connects the rotating port to a container and with a stationary member interfaced with the rotary member. The stationary member includes at least four stationary ports arranged in sequence in the direction of rotation of the rotating port. The first stationary port is elongated in the direction of and coincident with the arc path of the rotating port and is connected to a vacuum source. The second stationary port is small in length compared to the elongated ports and is coincident with the arc path of the rotating port and is positioned proximate the first elongated port and with the second port connected to a valve that normally directs vacuum to the port but may be actuated to direct a vacuum eliminator or abating means to the port. The third stationary port is elongated in the direction of and is coincident with the arc path of the rotating port and is positioned proximate the second port and connected to vacuum source. The fourth stationary port is small in length compared to the elongated port and is coincident with the arc path of the rotating port and is positioned proximate to the third port and is connected to a vacuum eliminator or abating means.

The size and position of the rotating and stationary ports are such that an uninterrupted flow of vacuum will be received by the rotating port as it rotates across the first three stationary ports, thus applying a positive vacuum to the container at all times as it is transferred from the beginning of the first port to the fourth port where it is released. In addition, the valve may be actuated, thus directing the vacuum eliminator means to the second port at the approximate time to release the container at the second port position.

The present invention is simple in construction and inexpensive in cost compared to the prior art devices and is relatively simple to maintain. A clearer understanding of the invention will be had with reference to the following description and drawings wherein:

Figure 1:
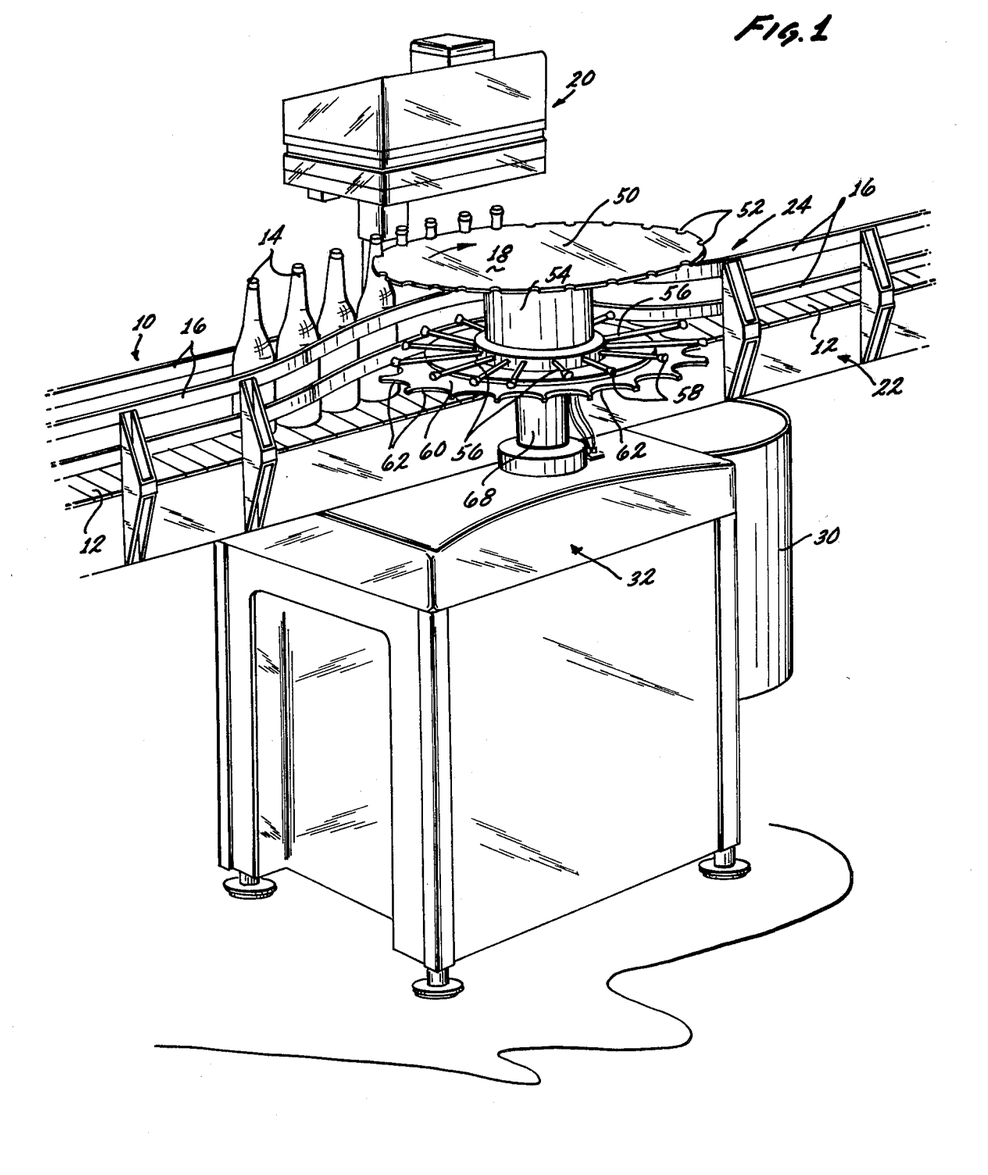
FIG. 1 illustrates a front perspective view of inspection equipment including a vacuum starwheel of the present invention.
Figure 2:
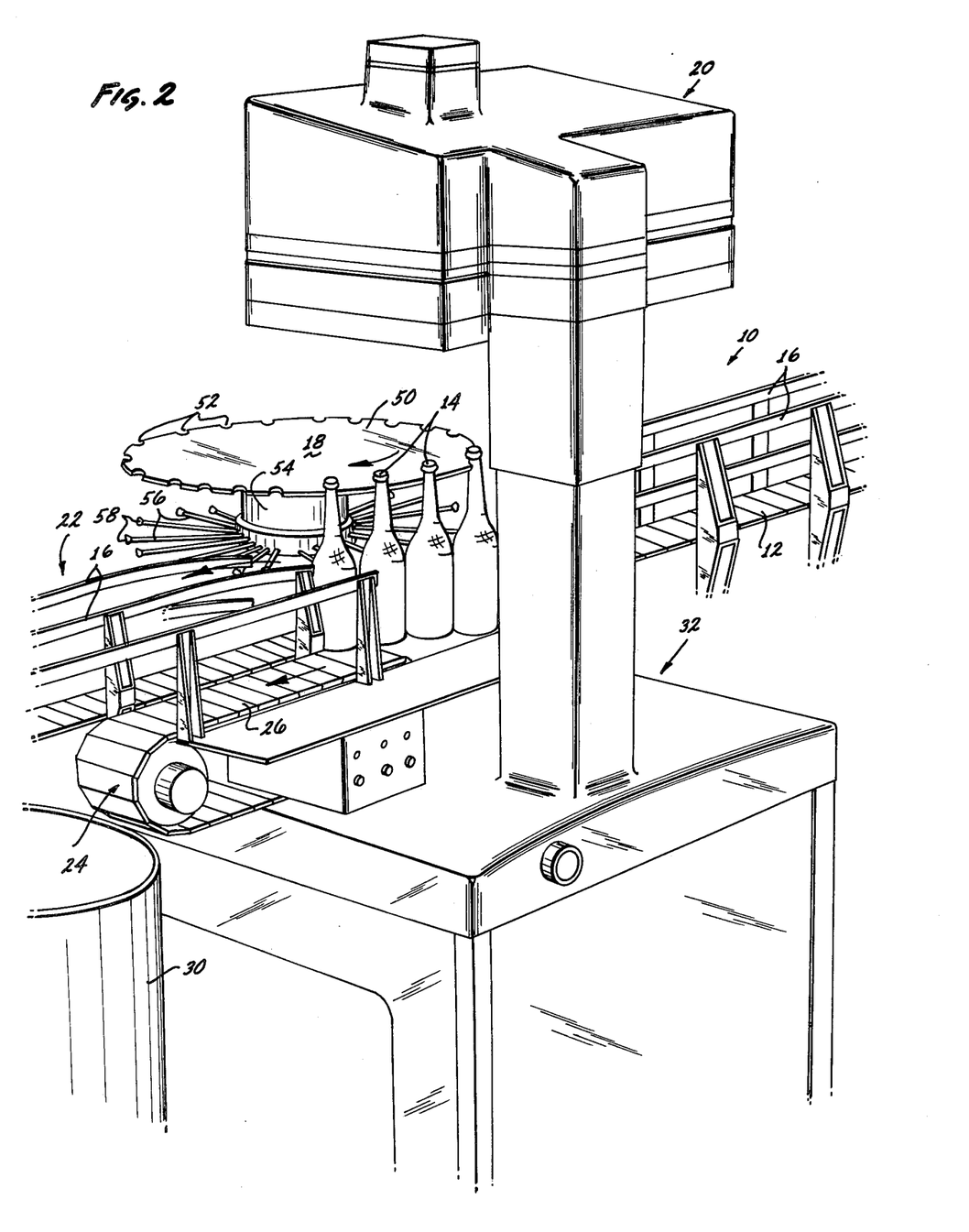
FIG. 2 illustrates a rear perspective view of the inspection equipment of FIG. 1.
Figure 13:
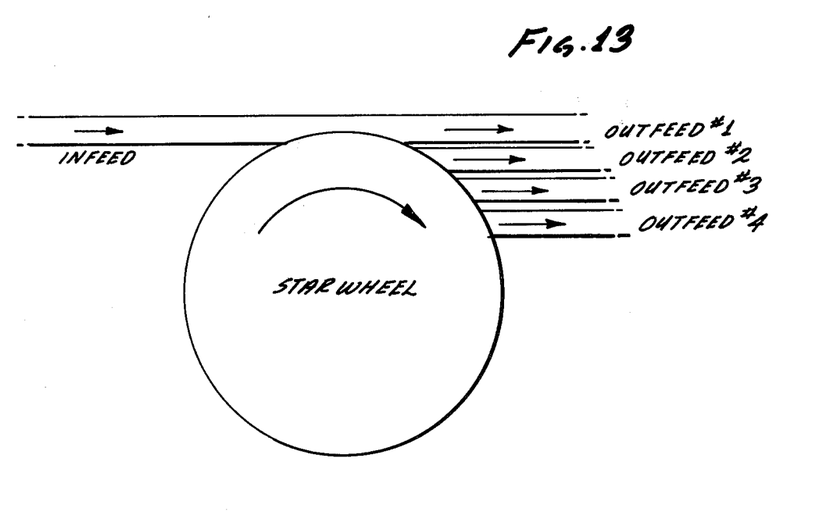
FIG. 13 illustrates a multiple outfeed system using the porting shown in FIG. 8.

FIGS. 1 and 2 show perspective views from the front and rear of a conveyor line passing by a bottle inspection station and including a vacuum starwheel of the present invention. The conveyor line includes an infeed conveyor line 10 having a conveyor belt 12 for conveying a plurality of containers, such as bottles 14. Rails 16 help to maintain the bottles in position during conveyance. The bottles 14 are guided by the rails 16 into a vacuum starwheel generally designated by reference numeral 18 and with the bottles 14 transferred off the conveyor line 10 by the vacuum starwheel 18 to pass by bottle inspection equipment 20. It is to be appreciated that although the invention is being disclosed with reference to using the vacuum starwheel to guide the bottles to a bottle inspection position, and with the acceptance and rejection of the bottle in accordance with the particular form of the inspection made by the bottle inspection equipment 20, the invention is not to be so limited. For example, the vacuum starwheel may be used to segregate the bottles in accordance with size or shape, or the vacuum starwheel may be used to merely subdivide the bottles coming from an infeed conveyor line to a plurality of outfeed conveyor lines as shown in FIG. 13. In addition, more than one infeed conveyor line may be used to feed the containers to the vacuum starwheel of the present invention.

In the particular use of the invention as shown in the present application, the bottle inspection equipment 20 provides a determination of a particular type of inspection to produce a control signal to control the vacuum starwheel 18 to either deposit the bottle inspected to one of two outfeed conveyors designated as outfeed conveyors 22 and 24. Specifically, outfeed conveyor 22 may actually be a continuation of infeed connector 10 and with the conveyor belt 12 extending below the vacuum starwheel 18 to form the conveyor belt for the outfeed conveyor 22. The outfeed conveyor 24 may be a short conveyor using a conveyor belt 26 and may represent a conveyor belt for rejected bottles and with the bottles passing off the conveyor belt to a reject pin 30. The outfeed conveyors 22 and 24 also include railings 16 for guiding the bottles in the outfeed lines.

When the bottle inspection equipment 20 provides the proper inspection, the bottle inspection equipment 20 produces the control signals which are fed to valving located in a control console 32 to provide for the proper control of pressure and vacuum to the vacuum starwheel 18 to deposit the bottles in either of the outfeed conveyors 22 and 24 in accordance with the inspection.

The vacuum starwheel 18 includes an upper rotating member 50 having a plurality of recesses 52 to support the neck portions of the bottles 14. The member 50 rotates along with a rotating hub 54. Extending from the rotating hub 54 are a plurality of tube members 56 each including a suction cup 58 at its end. The tubular members 56 transfer a vacuum or pressure from within the rotating hub 54 and from a source of vacuum or pressure within the console 32 to either hold the bottles 14 in engagement with the cups 58 or release the bottles from engagement with the cups. The tubes 56 and cups 58 are supported on the rotating hub 54 above a rotating starwheel 60 having pockets 62 to receive the body portion of the bottles 14. It can be seen, therefore, that the pockets 62 in the starwheel 60, the tubes 56 and the cups 58 and the recesses 52 in the number 50 are all in radial alignment and all rotate together with the rotation of hub 54.

Figure 5:
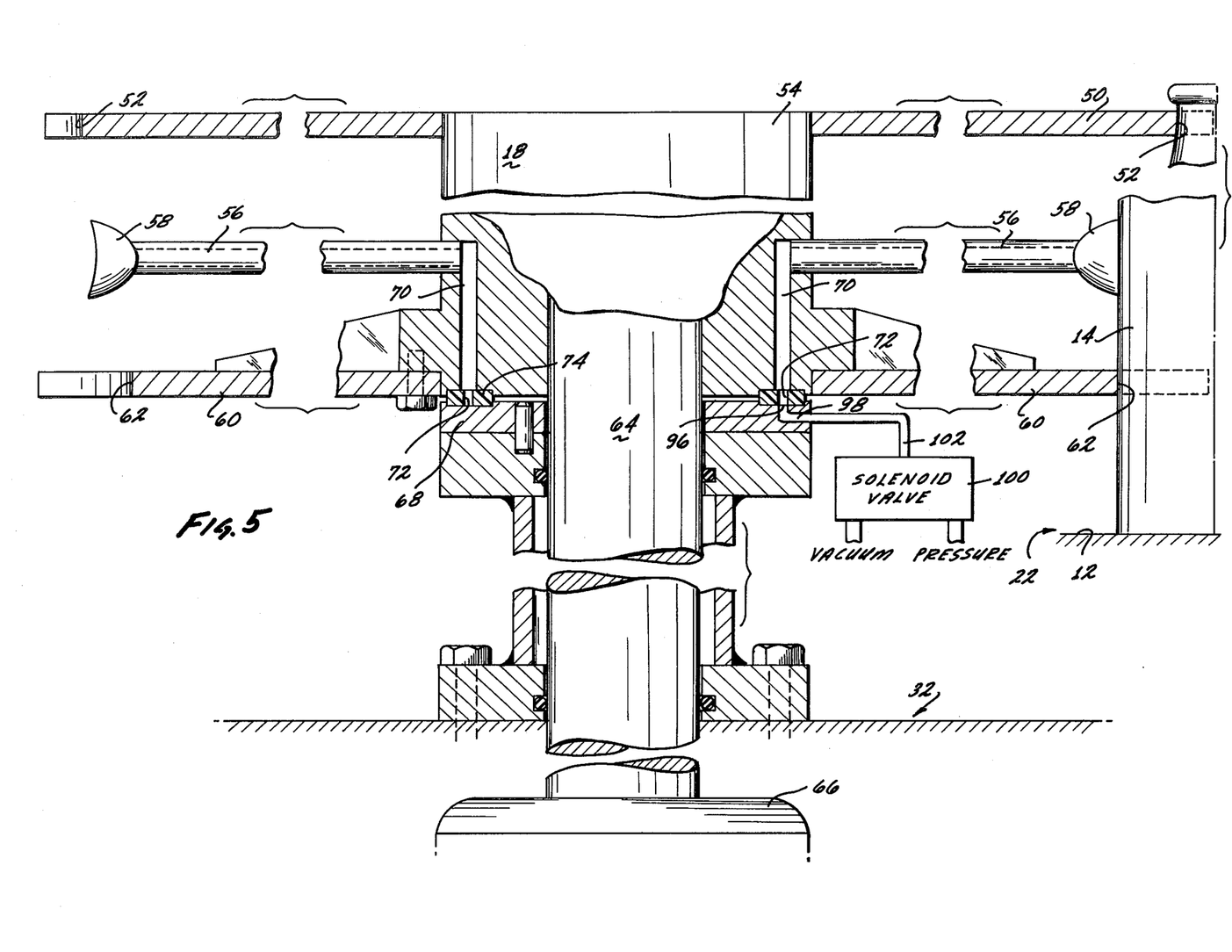
FIG. 5 illustrates a cross-sectional side view showing the stationary and rotating hubs.

As shown in FIG. 5 which illustrates the vacuum starwheel assembly 18 in cross-section, the rotating hub 54 is driven by a driveshaft 64 which driveshaft is rotated by a motor 66 supported by the console 32. As shown in FIG. 5, the rotating hub 54, the upper member 50, the tubes 56 and cups 58, the starwheel 60 all rotate together relative to a stationary hub 68. The driveshaft 64 passes through the stationary hub 68 which acts as a support and bearing housing but the driveshaft 64 does not provide any rotation of the stationary hub 68. The rotating hub 54 and stationary hub 68 are separated by a ring 74 of plastic, or suitable material, which operates as a bearing for the relative rotation between the two hub members and additionally provides for a sealing between the two members. This ring 74 is attached and sealed to the rotating hub 54.

Figure 4:
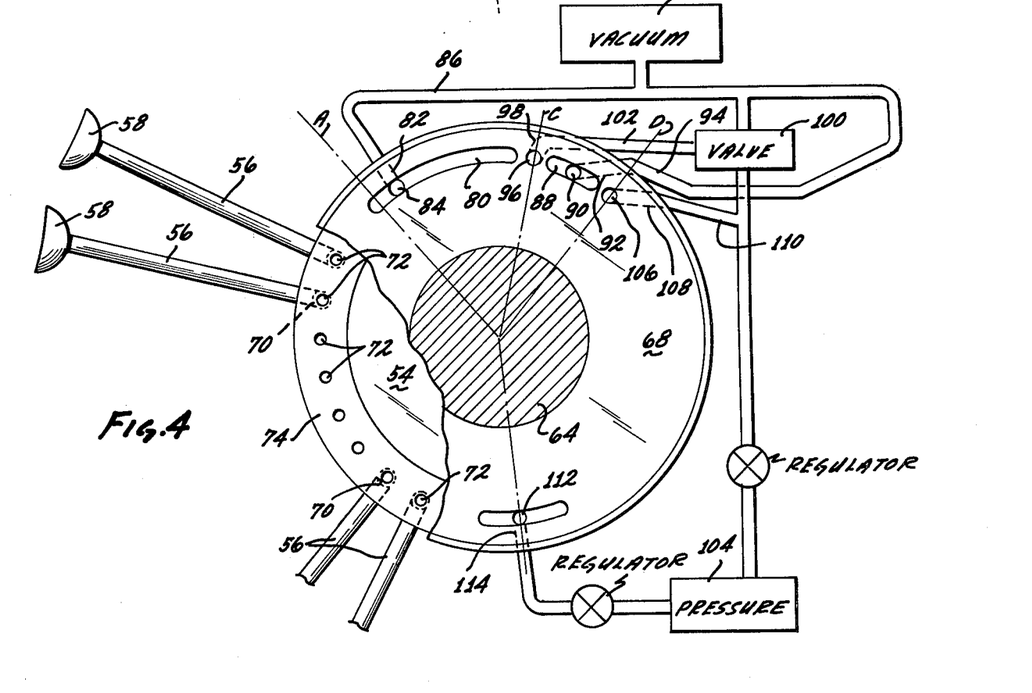
FIG. 4 illustrates the details of the porting in a stationary hub and in a rotating hub.

Referring to both FIGS. 4 and 5, it can be seen that the rotating hub 54 includes a plurality of internal cylindrical channels 70 which connect the tubes 56 down to a like number of small ports 72 in the ring 74, thus for each vacuum path there is a suction cup 58, tube 56, internal cylindrical channel 70 and a separate associated port 72. The ports 72 are positioned at a constant radial distance and equally spaced with respect to the center of the hub 54. This constitutes the porting arrangement of the rotating starwheel assembly 18.

Figure 6:
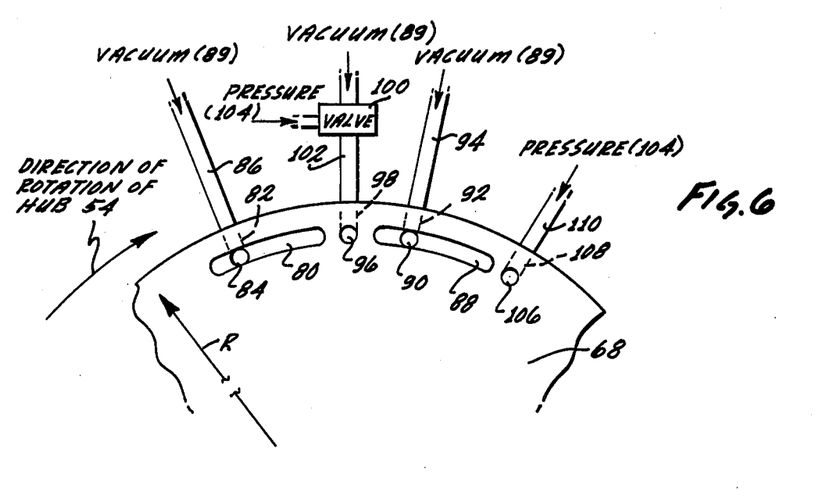
FIG. 6 illustrates a porting arrangement for a single line input with two outputs.

The stationary hub 68 has a porting arrangement on its top surface that establishes the segregating capabilities of the rotating starwheel assembly 18. A typical form of a recessed porting arrangement for the stationary hub 68 to accept a simple line input and separate it into two outputs is shown in FIG. 4 and with an alternative arrangement shown in FIG. 6. The recessed porting consists of a first elongated port 80, a first small port 96, a second elongated port 88 and a second small port 106. These ports are all positioned at the same constant radial distance as the ports 72 in the rotating hub 54. A constant vacuum source 89, which may be located inside the console 32, is connected to elongated port 80 via opening 84, internal hub channel 82 and pipe 86. Pipe 102 and internal hub channel 98 supplies port 96 with either vacuum or pressure from a reject selector valve 100. Pipe 94, internal hub channel 92 and opening 90 supplies elongated port 88 with vacuum from the same source as port 80. Pipe 110, internal hub channel 108 supplies port 106 with pressure. In the normal operating condition for this two channel segregator, valve 100 supplies vacuum to port 96. This constitutes the porting arrangement for the stationary hub 68.

Figure 9:
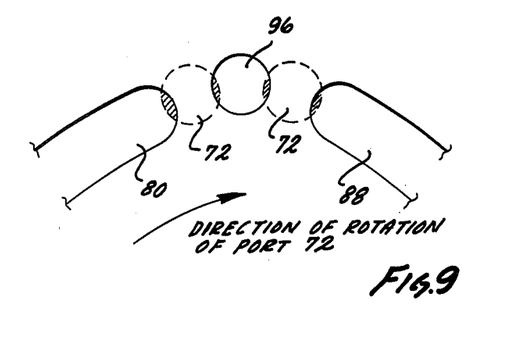
FIG. 9 illustrates the proper relative size between the rotating and the stationary ports.

As the rotating hub 54 rotates on top of the stationary hub 68, the ports 72 in the rotating hub 54 move sequentially over the ports 80, 96, 88 and 106 in the stationary hub 68. If any particular port 72 is traced in rotation as it moves across the fixed ports, a vacuum will be applied to the port 72 and its associated suction cup 58 as soon as its leading edge communicates with the leading edge of elongated port 80. This vacuum will continue to be applied until the trailing edge of the port 72 loses communication with the trailing edge of the port 80. Just prior to this position, however, the leading edge of the port 72 has communicated with the leading edge of port 96 which is a vacuum source, thus vacuum is never lost at the suction cup 58. FIG. 9 shows the required size and spacing dimensions between the elongated port 80 and the small port 96 as they relate to the rotating port 72. Rotating port 72 must slightly overlap (shaded area) both stationary ports 80 and 96 during the transition between them in order to maintain a constant vacuum supply to its associated suction cup. These same conditions are required of all other stationary port spacings. Vacuum will continue to be supplied to the port 72 until its trailing edge loses communication with the trailing edge of port 96, however, in this position the leading edge of the port 72 has communicated with the leading edge of the elongated port 88. Since port 88 is a source of vacuum, the port 72 will continue to receive vacuum until its trailing edge loses communication with the trailing edge of port 88. In this position, the leading edge of the port 72 communicates with the leading edge of the port 106 but, since port 106 is a pressure source, then port 72 directs this pressure into the internal channel 70, pipe 56 and suction cup 58, thus eliminating the vacuum from that cup. If a bottle was picked up by the suction cup 58 at the leading edge of port 80, it would be firmly held by a positive vacuum until it reached the leading edge of port 106 where it would be released.

Figure 10:
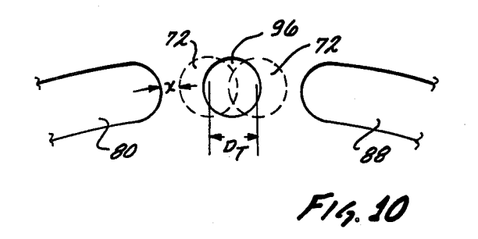
FIG. 10 illustrates the range over which the rotating port can receive a pressure pulse to release a container.
Figure 11:
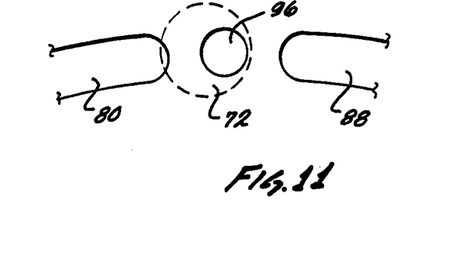
FIG. 11 illustrates a rotating port too large in size relative to the stationary ports.
Figure 12:
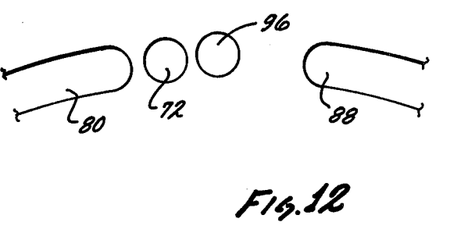
FIG. 12 illustrates a rotating port too small in size relative to the stationary ports.

If desired, the bottle could be released at port 96 by applying a pressure pulse from valve 100 at the appropriate time when the port 72 was over port 96. FIG. 10 shows the range $D_t$ where rotating port 72 can receive the pressure pulse without disturbing the rotating ports on either side. This arrangement allows an adequate time to eliminate the vacuum from the internal channel 70, pipe 56 and suction cup 58. It also results in a sufficient distance (x) between rotating port 72 and stationary ports 80 and 88 to insure a good seal. By the application of a pressure pulse at the appropriate time a bottle may be removed from the starwheel at port position 96 or, if no pressure pulse is applied, then the bottle will be removed at port position 106. The length of the elongated port essentially determines the distance the container is transported from the time it is picked up by the suction cup to the release point at the pressure reject port 96. The size of the small pressure 96 port does not alter the total transport distance appreciably since it is very small in size compared to the length of the elongated port. In practice, the minimum length of the elongated port is determined by the container diameter being handled. The elongated port must be of sufficient length to allow container clearance on the multiline output. Proper port size is necessary to accomplish a proper and reliable rejection sequence. FIG. 11 shows the rotating port 72 too large relative to the spacing between stationary ports 80 and 96 (or 96 and 88). This arrangement allows the pressure pulse from stationary port 96 to be directed into the vacuum port 80 and vice versa, which upsets the balance in the system causing malfunctions. FIG. 12 illustrates the difficulty encountered if the rotating port 72 is too small in size compared to the distance between the stationary ports 80 and 96 (or 96 and 88). In the position shown, rotating port 72 will receive no vacuum from any stationary port and, thus, could not apply the required constant vacuum to its associated suction cup.

Figure 7:
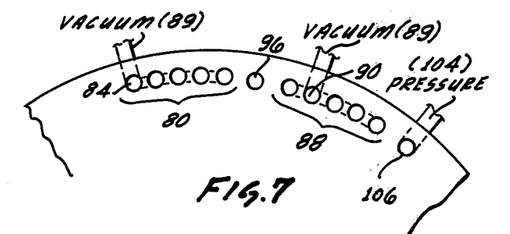
FIG. 7 illustrates an alternate arrangement for the elongated ports using a sequence of small holes.
Figure 8:
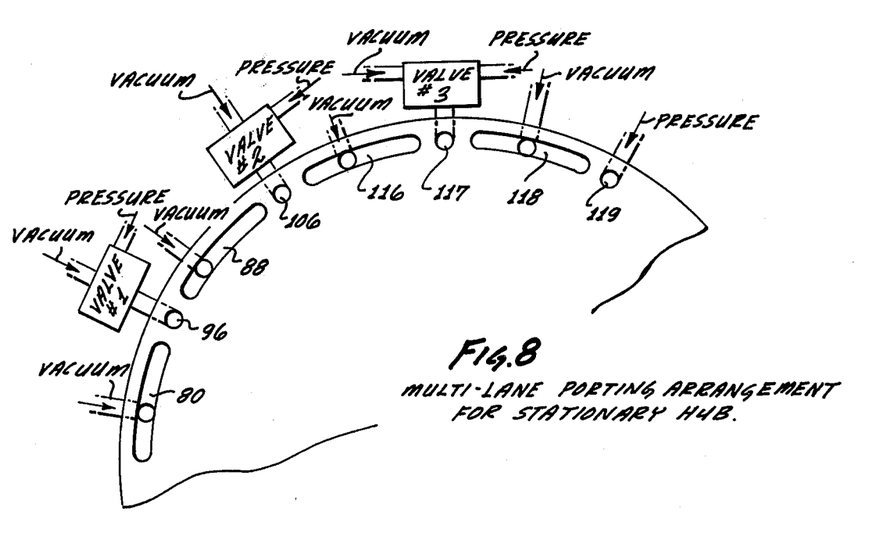
FIG. 8 illustrates a multiple porting arrangement.

It is obvious that more than two reject points can be used by adding additional ports and associated valves in the stationary hub 68. A porting configuration that segregates containers into four groups is shown in FIG. 8. This is the type of porting used with the system of FIG. 13. FIG. 7 shows an alternate method of constructing the elongated ports by using a closely spaced sequence of small holes connected below by a common vacuum chamber and it is to be appreciated that when the term "elongated port" is used, it includes an arrangement as shown in FIG. 7 or other similar arrangements.

The porting system as shown will operate if the ports 96 and 106 are directed to atmosphere instead of a pressure source such as an air compressor. The valve 100 may be an electric solenoid actuated air valve that directs the flow into the port. The release response time is slower if the ports are directed to atmosphere instead of a pressure source since it takes longer to eliminate the vacuum from the tubes and internal channels. For high-speed production lines the pressure pulse is the most desirable.

As the rotating hub 54 continues rotating, successive ones of the ports 72 will pass over an additional port 112 which is connected through an internal cylindrical channel 114 to the source of pressure 104. The pressure provides for purging successive ones of the ports 72, the internal cylindrical channels 70, the tubes 56 and the suction cups 58 of any extraneous matter which could clog these members.

Figure 3:
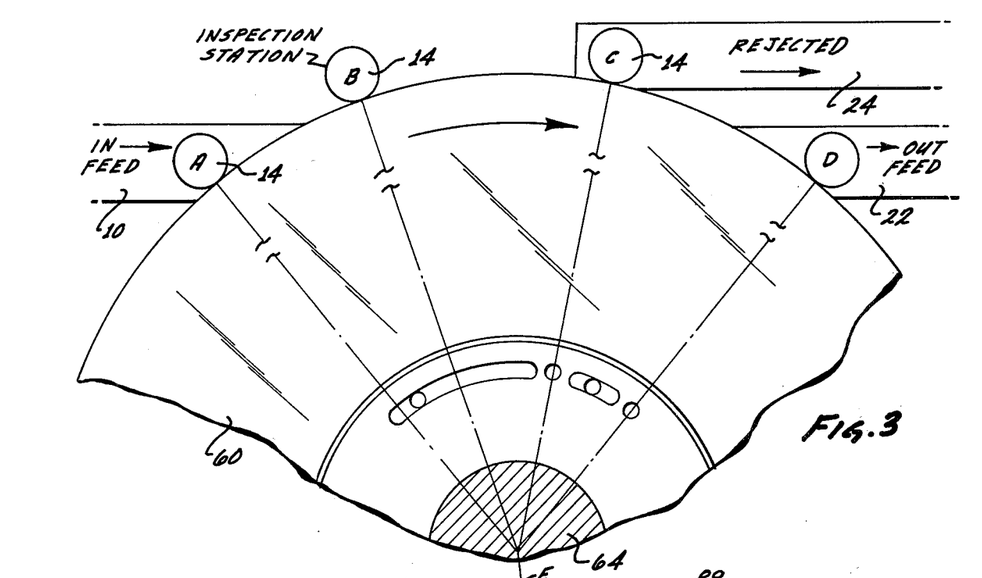
FIG. 3 illustrates in schematic form the various functions which occur as the container is moved through various positions by the vacuum starwheel.

Turning now to FIG. 3, a functional diagram shows the operation of the vacuum starwheel at a number of radial positions designated A through E. These radial positions correspond to the same radial positions shown in FIG. 4. As each bottle moves along the infeed conveyor 10, each bottle 14 engages a cup 58 at the end of a tube 56 and at position A vacuum is applied to hold the bottle against the cup and in the starwheel pocket so as to transport it off the conveyor for inspection. The bottle is passed through the inspection point B shown in FIG. 3 and is securely maintained in position since a positive vacuum is applied to the bottle throughout the transfer of the bottle.

If the bottle was faulty, the valve 100 shown in FIG. 4 is controlled to supply a pressure pulse at the appropriate time to the port 96 which is located at position C, and the bottle is positively released to the outfeed conveyor 24 to send the bottle to the reject bin 30 as shown in FIG. 1. If the bottle was good, then vacuum is maintained at position C which corresponds to the position of the port 96 and the bottle is transferred through position C and on to position D. The positive vacuum is applied at all times through the use of vacuum applied to the elongated ports 80 and 88 and to the port 96, all as shown in FIG. 4. At position D, the tube 56 and the cup 58 receive pressure from port 106 and the bottle is released to outfeed conveyor 22. As the rotating hub progresses, each particular port 72 is moved to position D where air pressure is supplied to purge the channels, tubes and cups to clean them of any debris.

It can be seen, therefore, that the present invention is directed to a vacuum starwheel which provides for a positive vacuum to hold containers, such as bottles, to maintain the bottles in position during transfer by the starwheel, and with the use of a pair of hub members, one rotating relative to the other, and with one hub member including a plurality of ports corresponding to and connecting with tubes and cups to retain the bottles and with the other hub including a plurality of ports connected to either vacuum, pressure or atmosphere, and with at least two of the ports being elongated, and with a first small port intermediate the two elongated ports, and with a second small port after the two elongated ports, and with vacuum always applied to the two elongated ports, and with either vacuum or pressure applied to the two small ports to either release a bottle at the intermediate position or to transfer the bottle along the entire length of the two elongated ports and then release the bottle. Although the application has been disclosed with reference to a particular embodiment, such as with bottle inspection equipment, it is to be appreciated that the invention is capable of various adaptations and modifications and the invention is only to be limited by the appended claims.

I claim:

1. A mechanism for transferring individual containers from one input position to one of at least two output positions, including:

a first member continuously movable in a particular path including at least one port and including means extending from the member and communicating with the port and constructed to retain one of the individual containers for movement with the first member when a vacuum is applied to the part, a second stationary member including at least first and second parts disposed in the path of movement of the first member for movement of the first port in the first member into sequential communication with the first and second ports in the second member, means defining a source of vacuum, means operatively coupled to the vacuum source and to the first and second ports in the second stationary member for producing vacuum in the first and second ports, the first and second ports in the second member being elongated in the path of movement of the first member and the length of the port in the first member being less than the length of the first and second ports in the second member to provide a vacuum with the retaining means in the first member for holding the container during the communication of the port in the first member with the ports in the first and second members, means for providing a source of at least atmospheric fluid pressure, the second stationary member including at least third and fourth ports disposed in the path of movement of the port in the first member for communication with the port in the first member at least a portion of the time during the movement of the first member, the third port being intermediate the first and second ports and the fourth port being positioned after the second port in the direction of movement of the port in the first member, the third port communicating with either the vacuum means or the pressure means, the fourth port communicating with the pressure means, the movable member providing a transfer of the individual container for release at the position of the third port when the third port communicates with the pressure means or for release at the position of the fourth port when the third port communicates with the vacuum means, the size of the first port in the first member in the path of movement of the first member being greater than the shortest distance between the second and third ports but less than the respective distance between the first or second ports and the side of the third port on the far side of the first and second ports in the path of movement of the first member, means for providing a continuous movement of the first member in the particular path, means for testing particular parameters on the container for particular characteristics during movement of the first member with the first port on the first member in communication with the first port on the second member at an intermediate position along the length of the first part, and means for providing a communication of the third port on the second member with a particular one of the vacuum means and the pressure means, in accordance with the characteristics of the particular parameters tested on the container by the testing means, during the communication of the first port on the first member only with the third port on the second member.

2. The vacuum transfer mechanism of claim 1 wherein the vacuum means communicates with the third port on the second member during the simultaneous positioning of the port on the first member with the first and third ports on the second member and during the simultaneous positioning of the port on the first member with the second and third ports on the second member.

3. The vacuum transfer mechanism of claim 2 additionally including a fifth port in the second member in the path of movement of the port on the first member and communicating with the pressure means to purge the mechanism when the port on the first member communicates with the fifth port on the second member.

4. The vacuum transfer mechanism of claim 1 wherein the first movable member is a rotatable hub including a starwheel having a plurality of pockets disposed in spaced relationship to one another around the periphery of the starwheel and wherein the containers are held in the starwheel pockets by vacuum and the path of movement of the port on the first member is annular and the first and second members have substantially planar surfaces disposed in contiguous relationship to one another and the respective ports in the first and second members are disposed in such planar surfaces.

5. The vacuum transfer mechanism of claim 1 additionally including at least one infeed conveyor for feeding the individual containers to the movable member and at least first and second outfeed conveyors to receive the individual containers from the movable member and the first outfeed conveyor being disposed to receive containers movable with the first member along the lengths of the first and second elongated ports in the second member to the position of the fourth port in the second member and the second outfeed conveyor being disposed to receive containers movable with the first member only along the length of the first elongated port in the second member to the position of the third port in the second member.

6. The vacuum transfer mechanism of claim 1 wherein each of the first and second elongated ports in the second member is at least partially formed from a plurality of closely spaced small ports.

7. A vacuum starwheel for transferring individual containers from one radial position to at least a second radial position, including, means for providing a vacuum, a continuously rotatable hub having a starwheel with pockets and including at least one port and including means extending from the rotatable hub and communicating with the port for retaining individual ones of the containers within individual ones of the pockets in the starwheel for movement with the rotatable hub upon the production of a vacuum in the port, a stationary hub including at least first and second ports disposed for communication with the port in the rotatable hub at least a portion of the time during the rotation of the rotatable hub, the first and second ports in the stationary hub communicating with the vacuum means, the first and second ports in the stationary hub being elongated in the direction of rotation of the rotatable hub and the length of the port in the rotary hub being less than the length of the first and second ports in the stationary hub to provide a vacuum for holding the container in one of the pockets in the starwheel during the communication of one of the first and second ports in the stationary hub with the port in the rotatable hub, means for providing at least atmospheric fluid pressure, the stationary hub including at least third and fourth ports disposed for communication with the port in the rotatable hub at least a portion of the time during the rotation of the rotatable hub, the third port being intermediate the first and second ports and the fourth port being disposed after the second port in the direction of rotation of the rotatable hub, the third port communicating with either the vacuum means or the pressure means, the fourth port communicating with the pressure means, the rotatable hub providing a transfer of the individual containers for release at the position of the third port when the port in the rotatable hub communicates only with the port in the rotatable hub and receives fluid pressure from the pressure means, the size of the port in the rotatable hub in the direction of rotation of the rotatable hub being greater than the distance between the first and third ports in the stationary hub and the distance between the second and third ports in the stationary hub but sufficiently small to provide a communication only with the third port in the stationary hub during a period of time when the port in the rotary hub is in communication with the third port in the stationary hub, the rotatable hub and the stationary hub being substantially planar and being disposed in contiguous relationship to each other along their substantially planar surfaces, and means for providing a communication with the third port in the stationary hub from only one of the vacuum means and the pressure means while the port in the rotatable hub is in communication only with the third port in the stationary hub and for providing a communication between the third port in the stationary hub and the vacuum means while the port in the rotatable hub is in communication simultaneously with the first and third ports in the stationary hub and simultaneously with the second and third ports in the stationary hub.

8. The vacuum starwheel of claim 7 wherein bearing means having low friction properties are disposed between the substantially planar surfaces of the rotatable hub and the stationary hub to inhibit fluid leakage.

9. The vacuum starwheel of claim 7 additionally including a fifth port in the stationary hub disposed in the stationary hub at a position after the fourth port along the direction of rotation of the continuously rotatable hub and communicating with the source of pressure to purge the vacuum starwheel of debris.

10. The vacuum starwheel of claim 7 wherein the rotatable hub including the starwheel includes a plurality of tubes corresponding in number to the number of pockets in the starwheel to transfer vacuum from the vacuum means to the pockets in the starwheel to hold the containers in the pockets and wherein means are provided for testing the containers for particular parameters and are activated with the port in the rotary hub at an intermediate position along the length of the first port and wherein means are provided for activating the pressure means, in accordance with the testing of the containers by the tesing means, when the port in the rotary hub is positioned solely over the third port in the stationary hub.

11. The vacuum starwheel of claim 7 additionally including at least one infeed conveyor for feeding the individual containers to the rotatable hub and at least two outfeed conveyors to receive the individual containers from the rotatable hub and a first one of the outfeed conveyors located to receive containers transferred along the path of the first and second elongated ports and through the third port to the position of the fourth port and a second one of the outfeed conveyors located to receive containers transferred only along the path of the first elongated port and to the position of the third port in accordance with the application of pressure from the pressure means to the third port when the port in the rotary hub is positioned solely over the third port in the stationary hub.

12. The vacuum starwheel of claim 7 wherein the first and second elongated ports are at least partially formed from a plurality of closely spaced ports.

13. A vacuum sorting mechanism for transferring individual containers from one infeed position to either of two independent outfeed positions, including, a rotary member continuously movable and having a plurality of spaced ports and corresponding radially extended holding means providing a communication between the ports to the individual containers, means for providing a source of vacuum, means for providing a source of at least atmospheric pressure, a stationary member interfaced with the rotary member and including four stationary ports arranged in sequence in the direction of rotation of the ports on the rotary member, the first stationary port being elongated in the direction of, and coicident with, the arc path of the ports in the rotary member and being communicative with the vacuum means, a valve having first and second positions, the second stationary port being coincident with the arc path of the ports in the rotary member and positioned proximate the first elongated port and responsive to the operation of the valve to communicate with the vacuum means in the first position of the valve and with the pressure means in the second position of the valve, the third stationary port being elongated in the direction of, and coincident with, the arc path of the ports in the rotary member and positioned proximate the second port and communicating with the vacuum means, the fourth stationary port being coincident with the arc path of the ports in the rotary member and positioned proximate to the third port and communicating with the pressure means, and the size and position of the ports in the rotary and stationary members providing for an uninterrupted production of vacuum in the ports in the rotary member as they rotate across the total arc distance from the beginning of the first port to the beginning of the fourth port with the valve in the first position for a transfer of the containers to the second outfeed position and a production of a pressure in the rotating ports as they rotate to the second port with the valve in the second position for a transfer of the containers to the first infeed position, the rotary and stationary members being substantially planar and disposed in contiguous relationship along their substantially planar surfaces.

14. A vacuum starwheel sorting mechanism for transporting individual containers from one infeed position to either of two independent outfeed positions, including, a rotary member continuously movable and having a starwheel with equally spaced pockets including an individual port for each pocket and suction cups and with the ports positioned on separate equally spaced radii at a substantially constant distance from the center of rotation of the rotary member, a stationary member interfaced with the rotary member and including four stationary ports positioned in sequence in the direction of rotation of the ports in the rotary member, means for providing air under at least atmospheric pressure, means for providing a vacuum, director means actuatable between first and second positions, the first port in the stationary member being elongated in the direction of, and coincident with, the arc path of the ports in the rotary member and being connected to the vacuum means, the second port in the stationary member being small in length compared to the first port and coincident with the arc path of the ports in the rotary member and positioned proximate the first elongated port and connected to the vacuum means with the director means in the first position and being connected to the pressure means with the director means in the second position, the third port in the stationary member being elongated in the direction of, and coincident with, the arc path of the ports in the rotary member and positioned proximate the second port and connected to the vacuum means, the fourth port in the stationary member being small in length compared to the elongated ports and coincident with the arc path of the ports in the rotary member and positioned proximate to the third port and connected to the pressure means, the ports in the stationary and rotary members being constructed to provide an uninterrupted vacuum in the ports in the rotary member as they move across the first three stationary ports to apply a vacuum to the individual containers at all times as they are transported by the starwheel from the beginning of the first port to the fourth port where they are released and the actuation of the second port director means providing for the introduction of a pressure from the pressure means to the second port at a particular time corresponding to a communication of one of the ports in the rotary member only with the second port to release at that position a particular individual container, the first and second members being provided with substantially planar surfaces disposed in contiguous relationship to each other, and the ports in the rotary member having a size to provide for the introduction of a vacuum from the vacuum means to such ports simultaneously from the first and second ports in the stationary member or simultaneously from the second and third ports in the stationary member and to provide for a communication of the ports in the rotary member only with the second port in the stationary member.

15. A vacuum sorting mechanism for transferring individual containers from one infeed position to either of two independent outfeed positions, including, a rotary member continuously movable and including at least one port and a corresponding radially extended holding means that connects the rotating port to an individual one of the containers a stationary member interfaced with the rotary member, the stationary member including four stationary ports arranged in sequence in the direction of rotation of the port in the rotary member, means for providing a vacuum, means for providing at least atmospheric pressure, the first port in the stationary member being elongated in the direction of, and coincident with, the arc path of the port in the rotary member and connected to the vacuum means, valve means having first and second positions, the second port in the stationary member being small in length compared to the first port and coincident with the arc path of the port in the rotary member and positioned proximate the first port and connected to the valve means to receive vacuum from the vacuum means with the valve in the first position and connected to receive a pressure from the pressure means with the valve means in the second position, the third port in the stationary member being elongated in the direction of, and coincident with, the arc path of the port in the rotary member and positioned proximate the second port and connected to the vacuum means, the fourth port in the stationary member being small in length compared to the elongated ports and coincident with the arc path of the port in the rotary member and positioned proximate the third port and connected to the pressure means, the ports in the rotary and stationary members providing for an uninterrupted flow of vacuum to the port in the rotary member as it rotates across the first three stationary ports to apply a vacuum to the individual container at all times as it is transferred from the beginning of the first port to the fourth port where it is released to the first of the two outfeed positions and to direct pressure from the pressure means to the second port in the stationary member, with the valve means in the second position at the positioning of the port in the rotary member solely in communication with the second port in the stationary member, to obtain a release of the individual container to the second of the two outfeed positions, means for normally retaining the valve means in the first position and for moving the valve means to the second position when the port in the rotary member is in communication only with the second port in the stationary member, the rotary and stationary members having substantially planer surfaces in contiguous relationship to each other and the ports in the rotary and stationary members extending through the substantially planer surfaces, and means for testing the individual container for a particular parameter with the port in the rotary member disposed at an intermediate position along the length of the first port in the stationary member and for obtaining an operation of the valve means in a particular one of the first and second positions, in accordance with such testing, with the port in the rotary member communicating only with the second port in the stationary member.

16. A vacuum sorting mechanism for transferring individual containers from one infeed position to any one of a number of independent outfeed positions, including a stationary member provided with a substantially planar surface, means for providing a vacuum, means for providing air under at least atmospheric pressure, a plurality of valve means each having first and second operative positions, a rotary member continuously movable and disposed in contiguous relationship with the substantially planar surface of the stationary member, the rotary member including a plurality of individual ports and corresponding radially extended holding means that connect each individual port in the rotary member to a particular one of the individual containers, with each port in the rotary member positioned a constant distance from the center of rotation of the rotary member, the stationary member including a number of sets of transfer/decision ports, corresponding to the number of outfeed positions, and said sets of ports being arranged in sequence in the direction of rotation of the ports in the rotary member and each transfer/decision set of ports consisting of at least two ports, the first transfer port in each set being elongated in the direction of, and coincident with, the arc path of the ports in the rotary member and connected to the vacuum means, the first decision port in each set being small in length compared to the first transfer port in the set and coincident with the arc path of the ports in the rotary member and positioned proximate the first transfer port in the set, said first decision port in each set being connected to an individual one of the valve means in the plurality to provide for the production of a vacuum in the first decision port with the associated valve means in the first position and the production of at least atmospheric pressure in the first decision port with the associated valve means in the second position, the size and position of the ports in the rotary and stationary member being such that an uninterrupted production of vacuum will be produced in the ports in the rotary members as they rotate across the stationary member spanning the total arc distance from the beginning of the first transfer port in the first set to the end of the last decision port in the last set, each of the valve means in the plurality being normally disposed in the first position and being actuated to the second position, the ports in the rotary and stationary members being constructed to provide for a bridging of the transfer and decision ports in each set by the associated one of the ports in the rotary member, means for providing for a movement of each of the valve means in the plurality to the second position when the associated one of the ports in the rotary member is in communication only with the associated decision port in the stationary member to obtain a transfer of individual containers in the plurality to individual ones of the outfeed stations, and means for testing each individual one of the containers during the movement of the associated one of the rotary parts at an intermediate position along the transfer port in the first set to control the operation of the valve means in the first and second positions in accordance with such testing.

17. In combination in a conveyor system for separating containers into first and second paths in accordance with the characteristics of a particular parameter in the containers, means for providing a continuous and uninterrupted conveyance of the containers in a particular path, means for providing a vacuum pressure, a first member movable in the particular path and constructed to receive vacuum pressures from the vacuum means and to provide forces at spaced positions on the periphery of the member for holding the containers for movement with the first member when vacuum pressures are provided at such spaced positions, the first member being provided with a plurality of ports spaced in the path of movement, means providing separate communications between individual ones of the ports in the first member and individual ones of the spaced positions on the periphery of the first member, a second member having first and second ports spaced from each other in the path of movement of the ports in the first member, the first port in the second member being elongated relative to the second port in the second member in the path of movement of the first member, means for introducing a vacuum from the vacuum pressure means to the first port in the second member, means for testing the characteristics of the particular parameter of each container during the continuous movement of the associated one of the ports on the first member in communication with the first port on the second member at an intermediate position along the length of the first port to produce a signal having first characteristics upon the occurrence of first characteristics in the particular parameter and a signal having second characteristics upon the occurrence of second characteristics in the particular parameter, means for providing air under at least atmospheric pressure, means for providing for the introduction of the air under at least atmospheric pressure from the pressure means into the second port on the second member, means for providing for the introduction of vacuum from the vacuum means into the second port on the second member, control means operatively coupled to the testing means, with each port in the first member in communication with only the second port in the second member, for obtaining the introduction of the vacuum to the second port in the second member upon the production of a signal with the first characteristics for the associated container and for obtaining the introduction of air under at least atmospheric pressure upon the production of a signal with the second characteristics for the associated container, means responsive to the introduction of a vacuum to the second port in the second member, with individual ones of the ports in the first member in communication with only the second port in the second member, for directing the associated containers in the first path, means responsive to the introduction of air under at least atmospheric pressure to the second port in the second member, with individual ones of the ports in the first member in communication with only the second port in the second member, for directing the associated containers in the second path, and means are provided for maintaining a vacuum in the second port in the second member during the movement of each of the ports in the first member at least partially in communication with the first port in the second member and wherein each of the ports in the first member has a length, in the path of movement of the first member, greater than the shortest distance between the first port and a near side of the second port in the second member but less than the distance between the first port and a far side of the second port in the second member.

18. The combination set forth in claim 17 wherein the control means are operative only while each of the ports in the first member is in communication with the second port in the second member without being in communication with the first port in the second member.

19. The combination set forth in claim 18 wherein the means directing the containers in the second path include a third port in the second member positioned after the first and second ports in the second member in the direction of movement of the ports in the first member and wherein means are provided for producing a vacuum from the vacuum means in the third port in the second member.

20. The combination set forth in claim 19 wherein the ports in the first member have a length, in the path of movement of the first member, greater than the shortest distance between the far side of the second port and the third port in the second member but less than the distance between the near side of the second port and the third port in the second member and wherein the control means are operative only while each of the ports in the first member is in communication with the second port in the second member without being in communication with the third port in the second member.

21. The combination set forth in claim 20 wherein the third port is disposed after the second port in the path of movement of the ports in the first member and wherein a fourth port is provided in the second member and is disposed after the third port in the path of movement of the ports in the first member and wherein means are provided for introducing air under pressure from the pressure means to the fourth port.

22. The combination set forth in claim 18 wherein the first and second members have substantially planar surfaces disposed in contiguous relationship to each other.

23. The vacuum transfer means of claim 4 wherein bearing means with lubricating properties are disposed between the first and second members to provide for a sealing between the members.

* * * * *